United States Patent [19]
Tiberi et al.

[11] Patent Number: 5,245,011
[45] Date of Patent: Sep. 14, 1993

[54] AQUEOUS SOLUTION CONTAINING $D_{1B}$ DOPAMINE RECEPTOR

[75] Inventors: Mario Tiberi; Keith R. Jarvie; Marc G. Caron, all of Durham, N.C.

[73] Assignee: Duke University, Durham, N.C.

[21] Appl. No.: 970,715

[22] Filed: Nov. 3, 1992

Related U.S. Application Data

[62] Division of Ser. No. 686,591, Apr. 16, 1991, Pat. No. 5,215,915.

[51] Int. Cl.$^5$ .................. C07K 13/00; C12N 15/12
[52] U.S. Cl. .................. 530/350; 435/64.1; 435/252.3; 435/320.1; 436/501
[58] Field of Search .............. 435/64.1, 252.3, 320.1; 530/350; 436/501

[56] References Cited

U.S. PATENT DOCUMENTS 4,859,609 8/1989 Dull et al. .......................... 436/501

FOREIGN PATENT DOCUMENTS

WO90/05780 5/1990 PCT Int'l Appl. .
WO91/06557 5/1991 PCT Int'l Appl. .

OTHER PUBLICATIONS

Biochemistry 27:3907-12 (1988) Gingrich et al, Affinity Chromatography of the $D_1$ Dopamine Receptor from Rat Corpus Striatum.
G. Sheppard *The Synaptic Organization of the Brain* 2d Ed., 268-288 (1979).
G. Sheppard *The Synaptic Organization of the Brain* 2d Ed., 308-337 (1979).
R. Hauptmann et al., *Nucleic Acids Research* 13, 4739-4749 (1985).
Yasuo Masu, et al.; *Nature* 329, 836-838 (1987) Oct.
Jeffrey L. Arriza, et al.; *Science* 237, 268-275 (1987) Jul.
Pierre Sokoloff, et al.; *Nature* 347, 146-151 (1990) Sep.
Frederick J. Monsma, Jr.; *Proc. Natl. Acad. Sci.* 87, 6723-6727 (1990) Sep.
Allen Dearry, et al., *Nature* 347, 72-76 (1990). Sep.
Qun-Yong Zhou et al., *Nature* 347, 76-80 (1990). Sep.
Roger K. Sunahara, et al. *Nature* 347, 80-83 (1990). Sep.
Lawrence C. Mahan et al., *Proc. Natl. Acad. Sci.* 87, 2196-2200 (1990).
Tiberi et al., *Proc. Natl. Acad. Sci. USA* 88, 7491-7495 (1991).

*Primary Examiner*—Robert J. Hill, Jr.
*Assistant Examiner*—John D. Ulm
*Attorney, Agent, or Firm*—Bell, Seltzer, Park & Gibson

[57] ABSTRACT

Disclosed is isolated DNA encoding a $D_{1B}$-dopamine receptor selected from the group consisting of: (a) isolated DNA which encodes rat $D_{1B}$-dopamine receptor; (b) isolated DNA which hybridizes to isolated DNA of (a) above and which encodes a $D_{1B}$-dopamine receptor; and (c) isolated DNA differing from the isolated DNAs of (a) and (b) above in codon sequence due to the degeneracy of the genetic code, and which encodes a $D_{1B}$ dopamine receptor. Vectors and host cells containing the same, assay procedures employing $D_{1B}$-dopamine receptors, oligonucleotide probes for identifying $D_{1B}$-dopamine receptors, and isolated and purified $D_{1B}$-dopamine receptors are also disclosed.

5 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:1:

```
AACCATGGAT  CCTACATCCC  TGTGGCCATC  ATGATTGTCA  CNTA                    4 4
```

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:2:

CCNCACAAAC ACACGACAAC CGATGGAAAG AAGCTTAAGA TCAAT                    45

( 2 ) INFORMATION FOR SEQ ID NO:3:

( i ) SEQUENCE CHARACTERISTICS:
( A ) LENGTH: 2308 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: N ( i v ) ANTI-SENSE: N ( i x ) FEATURE:
( A ) NAME/KEY: CDS
( B ) LOCATION: 694..2118
( D ) OTHER INFORMATION:

( x i ) SEQUENCE DESCRIPTION: SEQ ID NO:3:

| | | | | | |
|---|---|---|---|---|---|
| GAATTCAAGG | TCCTATGACC | CAGAATAGGG | GTTCGGGATA | CAGTTGTGAC | TTCGAAGGCC | 60 |
| ACTCTCCTAT | CCTCTAAGTC | TCTGGTTTGT | CTAGAGGCCT | CTGGATCTCC | TCCACCCAGA | 120 |
| AGTGTTCCAG | GAGAGACACC | AAGAGAGGTG | TTTGGGAGAA | GCTAATTCAT | GGGTTTGGGG | 180 |
| CAAGGGTGTG | GCACTGGGTT | CACTCTCGGA | CCTGTGTGTG | GCCTCTAAAG | TTGGAAGAAG | 240 |
| ACATCAGAGA | GTCATGAAGC | TAGGAAGCAG | GTGGGAGGGT | GCGCGGGCTG | CAGAAGCGTG | 300 |
| GCTGATAGGG | GCGGGCGCGC | GGGACGCGGC | AGCCACCGCG | CCAGAGAGAT | CGCCCGGTGC | 360 |
| CCGCGACTCC | GGACCCCGCC | CCCGTTGGCG | GCCGCTCTGC | GTTTCTCCGA | CTCGGAACCA | 420 |
| GACACAGTGG | CAGCCTCCGG | TGTGCTGCCG | ACACAGGATC | TCAGACCCGG | CGGCCCGCGG | 480 |
| GCATCGGTCG | TTTCTGGTCC | CATCTTGGGG | ACCAGAGGTG | CGCAAGAGTG | TTACCATTAC | 540 |
| AGGATCCTAA | GCGGTGCACG | GTGAGCGCTC | CTCGGGTCGG | GGACGGTCAG | CTGCAGGGCC | 600 |
| CGGACGACCT | CTGGGGTGGC | CGATGGGGCC | TTCCACGGGG | CGCAGGGGCG | AAGTTGGGAC | 660 |
| CGCAAGCAGA | GAGCCCGAGC | TACTCAGCGC | GAC ATG CTG CCT CCT GGG CGC AAC | | | 714 |

Met Leu Pro Pro Gly Arg Asn
1                   5

CGC ACG GCT CAA CCG GCA AGG CTG GGA TTA CAG AGG CAA CTG GCT CAG       762
Arg Thr Ala Gln Pro Ala Arg Leu Gly Leu Gln Arg Gln Leu Ala Gln
        10                  15                  20

GTG GAC GCC CCA GCG GGC TCT GCA ACC CCA CTG GGA CCC GCG CAG GTG       810
Val Asp Ala Pro Ala Gly Ser Ala Thr Pro Leu Gly Pro Ala Gln Val
    25                  30                  35

GTC ACC GCA GGC CTC CTG ACT CTC CTA ATC GTC TGG ACC TTG CTC GGG       858
Val Thr Ala Gly Leu Leu Thr Leu Leu Ile Val Trp Thr Leu Leu Gly
40                  45                  50                  55

AAC GTG CTA GTG TGT GCT GCC ATC GTC CGC AGC CGC CAT CTG CGC GCC       906
Asn Val Leu Val Cys Ala Ala Ile Val Arg Ser Arg His Leu Arg Ala
                60                  65                  70

AAG ATG ACC AAC ATC TTC ATC GTA TCC CTA GCT GTC TCA GAC CTC TTC       954
Lys Met Thr Asn Ile Phe Ile Val Ser Leu Ala Val Ser Asp Leu Phe
            75                  80                  85

GTG GCA TTG CTG GTC ATG CCC TGG AAG GCT GTG GCT GAG GTG GCT GGG       1002
Val Ala Leu Leu Val Met Pro Trp Lys Ala Val Ala Glu Val Ala Gly
        90                  95                  100

TAC TGG CCC TTT GGG ACA TTC TGC GAC ATC TGG GTG GCC TTT GAC ATC       1050
Tyr Trp Pro Phe Gly Thr Phe Cys Asp Ile Trp Val Ala Phe Asp Ile
    105                 110                 115

-continued

| | | | | | | | | | | | | | | | | |
|---|---|---|---|---|---|---|---|---|---|---|---|---|---|---|---|---|
| ATG | TGC | TCC | ACT | GCC | TCC | ATC | CTG | AAT | CTG | TGT | ATC | ATC | AGC | GTG | GAC | 1098 |
| Met 120 | Cys | Ser | Thr | Ala | Ser 125 | Ile | Leu | Asn | Leu | Cys 130 | Ile | Ile | Ser | Val | Asp 135 | |
| CGT | TAC | TGG | GCT | ATT | TCC | AGA | CCC | TTC | CGC | TAC | GAG | CGC | AAG | ATG | ACC | 1146 |
| Arg | Tyr | Trp | Ala | Ile 140 | Ser | Arg | Pro | Phe | Arg 145 | Tyr | Glu | Arg | Lys | Met 150 | Thr | |
| CAG | CGA | GTA | GCC | CTG | GTC | ATG | GTG | GGC | CTG | GCC | TGG | ACC | TTG | TCC | ATC | 1194 |
| Gln | Arg | Val | Ala 155 | Leu | Val | Met | Val | Gly 160 | Leu | Ala | Trp | Thr | Leu 165 | Ser | Ile | |
| CTC | ATC | TCC | TTC | ATC | CCG | GTC | CAA | CTC | AAT | TGG | CAC | AGA | GAC | AAG | GCA | 1242 |
| Leu | Ile | Ser 170 | Phe | Ile | Pro | Val | Gln 175 | Leu | Asn | Trp | His | Arg 180 | Asp | Lys | Ala | |
| GGC | TCC | CAG | GGC | CAA | GAG | GGC | CTG | CTG | TCC | AAT | GGG | ACA | CCC | TGG | GAG | 1290 |
| Gly | Ser | Gln 185 | Gly | Gln | Glu | Gly | Leu 190 | Leu | Ser | Asn | Gly | Thr 195 | Pro | Trp | Glu | |
| GAA | GGC | TGG | GAG | CTA | GAA | GGG | AGG | ACG | GAG | AAC | TGT | GAC | TCC | AGC | CTG | 1338 |
| Glu 200 | Gly | Trp | Glu | Leu | Glu 205 | Gly | Arg | Thr | Glu | Asn 210 | Cys | Asp | Ser | Ser | Leu 215 | |
| AAC | CGA | ACC | TAT | GCC | ATC | TCC | TCG | TCA | CTC | ATC | AGC | TTC | TAC | ATC | CCG | 1386 |
| Asn | Arg | Thr | Tyr | Ala 220 | Ile | Ser | Ser | Ser | Leu 225 | Ile | Ser | Phe | Tyr | Ile 230 | Pro | |
| GTG | GCC | ATC | ATG | ATC | GTG | ACC | TAT | ACG | CGT | ATC | TAC | CGC | ATT | GCG | CAG | 1434 |
| Val | Ala | Ile | Met 235 | Ile | Val | Thr | Tyr | Thr | Arg 240 | Ile | Tyr | Arg | Ile | Ala 245 | Gln | |
| GTG | CAG | ATC | CGG | CGG | ATC | TCC | TCC | CTA | GAG | AGG | GCA | GCT | GAG | CAT | GCT | 1482 |
| Val | Gln | Ile | Arg 250 | Arg | Ile | Ser | Ser | Leu 255 | Glu | Arg | Ala | Ala | Glu 260 | His | Ala | |
| CAG | AGT | TGC | CGG | AGT | CGT | GGA | GCC | TAT | GAA | CCT | GAC | CCC | AGC | CTG | CGA | 1530 |
| Gln | Ser | Cys 265 | Arg | Ser | Arg | Gly | Ala 270 | Tyr | Glu | Pro | Asp | Pro 275 | Ser | Leu | Arg | |
| GCG | TCC | ATC | AAG | AAG | GAG | ACC | AAG | GTC | TTC | AAA | ACC | CTG | TCA | ATG | ATC | 1578 |
| Ala 280 | Ser | Ile | Lys | Lys | Glu 285 | Thr | Lys | Val | Phe | Lys 290 | Thr | Leu | Ser | Met | Ile 295 | |
| ATG | GGG | GTC | TTC | GTG | TGT | TGC | TGG | TTG | CCT | TTC | TTC | ATC | CTG | AAC | TGT | 1626 |
| Met | Gly | Val | Phe | Val 300 | Cys | Cys | Trp | Leu | Pro 305 | Phe | Phe | Ile | Leu | Asn 310 | Cys | |
| ATG | GTT | CCT | TTC | TGC | AGT | AGT | GGG | GAT | GCC | GAG | GGC | CCA | AAG | ACT | GGC | 1674 |
| Met | Val | Pro | Phe 315 | Cys | Ser | Ser | Gly | Asp 320 | Ala | Glu | Gly | Pro | Lys 325 | Thr | Gly | |
| TTC | CCT | TGT | GTC | AGC | GAG | ACC | ACC | TTC | GAC | ATA | TTC | GTC | TGG | TTT | GGC | 1722 |
| Phe | Pro | Cys 330 | Val | Ser | Glu | Thr | Thr 335 | Phe | Asp | Ile | Phe | Val 340 | Trp | Phe | Gly | |
| TGG | GCG | AAC | TCC | TCT | CTC | AAT | CCC | ATC | ATC | TAT | GCC | TTT | AAT | GCA | GAC | 1770 |
| Trp | Ala | Asn 345 | Ser | Ser | Leu | Asn 350 | Pro | Ile | Ile | Tyr | Ala 355 | Phe | Asn | Ala | Asp | |
| TTC | CGG | AAG | GTG | TTT | GCC | CAG | CTG | CTG | GGG | TGC | AGC | CAC | TTC | TGC | TTC | 1818 |
| Phe | Arg 360 | Lys | Val | Phe | Ala | Gln 365 | Leu | Leu | Gly | Cys | Ser 370 | His | Phe | Cys | Phe 375 | |
| CGG | ACC | CCA | GTG | CAG | ACG | GTA | AAC | ATC | AGT | AAT | GAG | CTC | ATC | TCC | TAC | 1866 |
| Arg | Thr | Pro | Val | Gln 380 | Thr | Val | Asn | Ile | Ser 385 | Asn | Glu | Leu | Ile | Ser 390 | Tyr | |
| AAC | CAA | GAC | ACG | GTC | TTC | CAC | AAG | GAG | ATC | GCT | ACT | GCC | TAT | GTC | CAC | 1914 |
| Asn | Gln | Asp | Thr 395 | Val | Phe | His | Lys | Glu 400 | Ile | Ala | Thr | Ala | Tyr 405 | Val | His | |
| ATG | ATA | CCG | AAT | GCA | GTA | TCC | TCC | GGA | GAC | AGG | GAG | GTG | GGA | GAG | GAG | 1962 |
| Met | Ile | Pro | Asn 410 | Ala | Val | Ser | Ser | Gly 415 | Asp | Arg | Glu | Val | Gly 420 | Glu | Glu | |
| GAG | GAG | GAG | GGG | CCT | TTC | GAT | CAC | ATG | TCT | CAA | ATC | TCT | CCA | ACG | ACG | 2010 |
| Glu | Glu | Glu 425 | Gly | Pro | Phe | Asp | His 430 | Met | Ser | Gln | Ile | Ser 435 | Pro | Thr | Thr | |
| CCA | GAC | GGT | GAC | CTG | GCT | GCT | GAG | TCT | GTC | TGG | GAG | CTT | GAC | TGT | GAG | 2058 |
| Pro | Asp | Gly | Asp | Leu | Ala | Ala | Glu | Ser | Val | Trp | Glu | Leu | Asp | Cys | Glu | |

-continued

```
        440                 445                 450                 455
GAA GAG GTT TCC  TTA GGC AAA ATC  TCA CCT CTC ACC  CCC AAT TGT TTC         2106
Glu Glu Val Ser  Leu Gly Lys Ile  Ser Pro Leu Thr  Pro Asn Cys Phe
             460              465              470

GAT AAA ACT GCT  TAGAAACATT CTCATGGGCA TATACAATGG TGGCCATATT               2158
Asp Lys Thr Ala
             475

TCCAAGCATG CACAAATACC CACGTGCGTA CACACACACA CACACACACA CACACACACA          2218

CACACACTCC AGTGTGCATA TGCTTTCTGT AGTCTGCTGC ATAGAAACAA ACGATTCTTA          2278

GCTGAGAAAT GACGAGGCTG TTGGATAACT                                           2308
```

( 2 ) INFORMATION FOR SEQ ID NO:4:

( i ) SEQUENCE CHARACTERISTICS:
            ( A ) LENGTH: 475 amino acids
            ( B ) TYPE: amino acid
            ( D ) TOPOLOGY: linear ( i i ) MOLECULE TYPE: protein ( x i ) SEQUENCE DESCRIPTION: SEQ ID NO:4:

```
Met Leu Pro Pro  Gly Arg Asn Arg  Thr Ala Gln Pro  Ala Arg Leu Gly
 1               5                    10                   15

Leu Gln Arg Gln  Leu Ala Gln Val  Asp Ala Pro Ala  Gly Ser Ala Thr
             20                   25                   30

Pro Leu Gly Pro  Ala Gln Val Val  Thr Ala Gly Leu  Leu Thr Leu Leu
             35                   40                   45

Ile Val Trp Thr  Leu Leu Gly Asn  Val Leu Val Cys  Ala Ala Ile Val
 50                  55                   60

Arg Ser Arg His  Leu Arg Ala Lys  Met Thr Asn Ile  Phe Ile Val Ser
 65              70                   75                       80

Leu Ala Val Ser  Asp Leu Phe Val  Ala Leu Leu Val  Met Pro Trp Lys
                 85                   90                       95

Ala Val Ala Glu  Val Ala Gly Tyr  Trp Pro Phe Gly  Thr Phe Cys Asp
             100                  105                  110

Ile Trp Val Ala  Phe Asp Ile Met  Cys Ser Thr Ala  Ser Ile Leu Asn
             115                  120                  125

Leu Cys Ile Ile  Ser Val Asp Arg  Tyr Trp Ala Ile  Ser Arg Pro Phe
 130                 135                  140

Arg Tyr Glu Arg  Lys Met Thr Gln  Arg Val Ala Leu  Val Met Val Gly
 145                 150                  155                      160

Leu Ala Trp Thr  Leu Ser Ile Leu  Ile Ser Phe Ile  Pro Val Gln Leu
             165                  170                  175

Asn Trp His Arg  Asp Lys Ala Gly  Ser Gln Gly Gln  Glu Gly Leu Leu
             180                  185                  190

Ser Asn Gly Thr  Pro Trp Glu Glu  Gly Trp Glu Leu  Glu Gly Arg Thr
             195                  200                  205

Glu Asn Cys Asp  Ser Ser Leu Asn  Arg Thr Tyr Ala  Ile Ser Ser Ser
             210                  215                  220

Leu Ile Ser Phe  Tyr Ile Pro Val  Ala Ile Met Ile  Val Thr Tyr Thr
 225                 230                  235                      240

Arg Ile Tyr Arg  Ile Ala Gln Val  Gln Ile Arg Arg  Ile Ser Ser Leu
                 245                  250                  255

Glu Arg Ala Ala  Glu His Ala Gln  Ser Cys Arg Ser  Arg Gly Ala Tyr
             260                  265                  270

Glu Pro Asp Pro  Ser Leu Arg Ala  Ser Ile Lys Lys  Glu Thr Lys Val
             275                  280                  285
```

```
Phe  Lys  Thr  Leu  Ser  Met  Ile  Met  Gly  Val  Phe  Val  Cys  Cys  Trp  Leu
     290                      295                300

Pro  Phe  Phe  Ile  Leu  Asn  Cys  Met  Val  Pro  Phe  Cys  Ser  Ser  Gly  Asp
305                      310                315                          320

Ala  Glu  Gly  Pro  Lys  Thr  Gly  Phe  Pro  Cys  Val  Ser  Glu  Thr  Thr  Phe
               325                     330                          335

Asp  Ile  Phe  Val  Trp  Phe  Gly  Trp  Ala  Asn  Ser  Ser  Leu  Asn  Pro  Ile
               340                     345                     350

Ile  Tyr  Ala  Phe  Asn  Ala  Asp  Phe  Arg  Lys  Val  Phe  Ala  Gln  Leu  Leu
          355                     360                     365

Gly  Cys  Ser  His  Phe  Cys  Phe  Arg  Thr  Pro  Val  Gln  Thr  Val  Asn  Ile
     370                     375                     380

Ser  Asn  Glu  Leu  Ile  Ser  Tyr  Asn  Gln  Asp  Thr  Val  Phe  His  Lys  Glu
385                      390                     395                          400

Ile  Ala  Thr  Ala  Tyr  Val  His  Met  Ile  Pro  Asn  Ala  Val  Ser  Ser  Gly
               405                     410                          415

Asp  Arg  Glu  Val  Gly  Glu  Glu  Glu  Glu  Glu  Gly  Pro  Phe  Asp  His  Met
               420                     425                     430

Ser  Gln  Ile  Ser  Pro  Thr  Thr  Pro  Asp  Gly  Asp  Leu  Ala  Ala  Glu  Ser
          435                     440                     445

Val  Trp  Glu  Leu  Asp  Cys  Glu  Glu  Glu  Val  Ser  Leu  Gly  Lys  Ile  Ser
     450                     455                     460

Pro  Leu  Thr  Pro  Asn  Cys  Phe  Asp  Lys  Thr  Ala
465                      470                     475
```

AQUEOUS SOLUTION CONTAINING $D_{1B}$ DOPAMINE RECEPTOR

This invention was made with Government support under Grant No. NS19576 from the National Institutes of Health. The Government may have certain rights to this invention.

This application is a division of pending application Ser. No. 07/686,591, filed Apr. 16, 1991 now U.S. Pat. No. 5,215,915.

BACKGROUND OF THE INVENTION

Dopamine exerts its physiological actions in the periphery as well as in the central nervous system (CNS) by interacting with multiple dopaminergic receptors. Recently, molecular biological approaches have established that the effects of dopamine in the CNS are mediated by at least three different receptors, namely $D_1$, $D_2$ and $D_3$. See A. Dearry et al., Nature 347, 72–76 (1990); Q.-Y. Zhou et al., Nature 347, 76–80 (1990); R. Sunahara et al., Nature 347, 80–83 (1990); F. Monsma et al., Proc. Natl. Acad. Sci. USA s7, 6723–6727 (1990); J. Bunzow et al., Nature 336, 783–787 (1988); B. Giros et al., Nature 342, 923–926 (1989); F. Monsma, et al., Nature 342, 926–929 (1989); P. Sokoloff et al., Nature 347, 146–151 (1990). The genes encoding these receptors are distinct but homologous and belong to the large family of receptors coupled to guanine nucleotide regulatory protein (G protein). See B. O'Dowd et al., Ann. Rev. Neurosci. 12, 67–83 (1989). One major feature of these receptors is that they contain seven putative membrane spanning domains in their structure.

The actions of dopamine were originally thought to be mediated by an interaction with two distinct receptor subtypes: $D_1$ receptors which were coupled to the stimulation of adenylyl cyclase and $D_2$ receptors which were either uncoupled or coupled to the inhibition of adenylyl cyclase. See J. Kebabian and D. Calne, Nature 277, 93–96 (1979). More recently, it has become apparent that multiple $D_1$ receptors may exist. See P. Andersen et al., Trends Pharmacol. Sci. 11, 231–236 (1990]. For instance, it has been demonstrated that injection of rat striatal mRNA into Xenopus oocytes directs the expression of a $D_1$ dopamine receptor coupled to activation of phospholipase C and this activation leads to inositol phosphate (IPs) accumulation in injected eggs. L. Mahan et al., Proc. Natl. Acad. Sci. USA 87, 2196–2200 (1990). Furthermore, dopamine does not stimulate adenylyl cyclase in the amygdala, a tissue known to contain specific binding sites for the radiolabeled $D_1$-selective antagonist SCH 23390. P. Andersen et al., supra. In the periphery, $D_1$ receptors have been shown to stimulate adenylyl cyclase as well as phospholipase C. See E. Baldi al., Eur. J. Pharmacol. 149, 351–356 (1988); C. Missale et al., J. Cardiovasc. Pharmacol. 11, 643–650 (1985); C. Felder et al., J. Pharmacol. Exp. Ther. 248, 171–175 (1989). Moreover, peripheral $D_1$ receptors differ pharmacologically from their CNS counterparts. Using the cloned human $D_1$ receptor as a probe, we have reported that multiple hybridizing bands on Southern blot analysis at low stringency could be observed. This finding is consistent with the presence of other closely related receptors. A. Dearry et al., supra.

In the patent literature, a cloned gene encoding a mammalian $D_2$-dopamine receptor is reported in O. Civelli et al., PCT Patent Application WO 90/05780. A cloned gene encoding a mammalian $D_1$-dopamine receptor is described in J. Bunzow et al., Pending U.S. patent application Ser. No. 07/583,852, filed Sep. 17, 1990 now abandoned. Insofar as these applicants are aware, no distinct subtypes of $D_1$-dopamine receptors have previously been disclosed.

SUMMARY OF THE INVENTION

We now report the cloning of a new $D_1$ receptor subtype, the $D_{1B}$-dopamine receptor, which is strikingly different from the previously cloned $D_1$ receptor in its mRNA distribution.

A first aspect of the present invention is isolated DNA encoding a $D_{1B}$-dopamine receptor selected from the group consisting of: (a) isolated DNA which encodes rat $D_{1B}$-dopamine receptor; (b) isolated DNA which hybridizes to isolated DNA of (a) above and which encodes a $D_{1B}$-dopamine receptor; and (c) isolated DNA differing from the isolated DNAs of (a) and (b) above in codon sequence due to the degeneracy of the genetic code, and which encodes a $D_{1B}$ dopamine receptor.

A second aspect of the present invention is a recombinant DNA sequence comprising vector DNA and a DNA encoding a $D_{1B}$-dopamine receptor as given above.

A third aspect of the present invention is a host cell containing a recombinant DNA sequence as given above.

A fourth aspect of the present invention is an aqueous solution containing cell membranes, said cell membranes containing a $D_{1B}$-dopamine receptor, wherein said cell membranes are free of $D_{1A}$-dopamine receptors. The cell membranes may further contain adenylyl cyclase, with the $D_{1B}$-dopamine receptors capable of stimulating the adenylyl cyclase on binding a $D_{1B}$-dopamine receptor agonist. The cell membranes are also preferably provided free of $D_2$-dopamine receptors and any other dopamine receptor subtypes.

A fifth aspect of the present invention is an assay procedure comprising the steps of, first, providing an aqueous solution containing cell membranes as given above; then adding a test compound to the aqueous solution; and then monitoring the binding of the test compound to the $D_{1B}$ dopamine receptors.

A sixth aspect of the present invention is an oligonucleotide probe capable of selectively hybridizing to a DNA comprising a portion of a gene coding for a $D_{1B}$-dopamine receptor, which probe does not hybridize to a gene coding for a $D_{1A}$-dopamine receptor.

A seventh aspect of the present invention is isolated and purified $D_{1B}$-dopamine receptor which is coded for by DNA selected from the group consisting of: (a) isolated DNA which encodes rat $D_{1B}$-dopamine receptor; (b) isolated DNA which hybridizes to isolated DNA of (a) above and which encodes a $D_{1B}$-dopamine receptor; and (c) isolated DNA differing from the isolated DNAs of (a) and (b) above in codon sequence due to the degeneracy of the genetic code, and which encodes a $D_{1B}$ dopamine receptor.

DETAILED DESCRIPTION OF THE INVENTION

Figure 1:
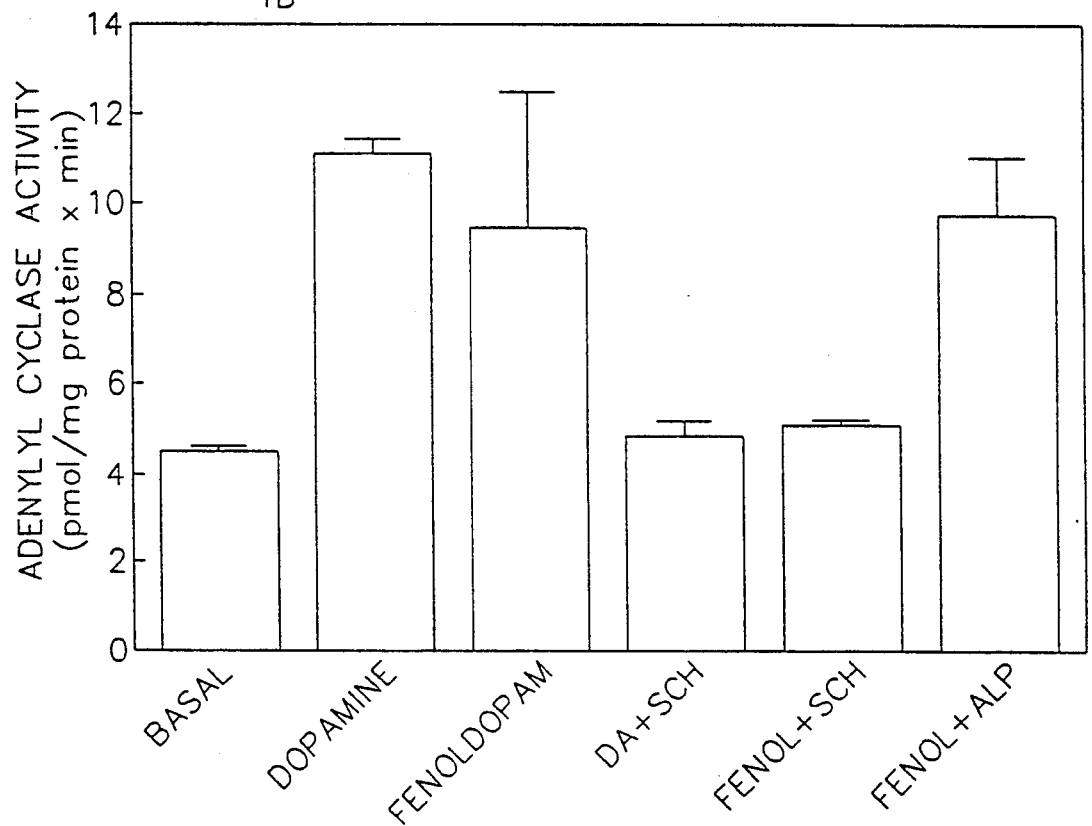
FIG. 1. Stimulation of adenylyl cyclase in membranes prepared from 293 cells transfected with pCMV5-DR5expression construct. Results are the mean±s.e.m. of a representative example of two independent experiments done in triplicate determinations. Drugs and concentrations used are dopamine (DA), 100 $\mu$M; fenoldopam (FENOL), 1 μM; SCH 23390 (SCH), 1 μM; and alprenolol (ALP), 1 μM.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., Patentin User Manual, 99-102 (Nov. 1990) (U.S. Patent and Trademark Office, Office of the Assistant Commissioner for Patents, Washington, D.C. 20231); U.S. Pat. No. 4,871,670 to Hudson et al. at Col. 3 lines 20-43 (applicants specifically intend that the disclosure of this and all other patent references cited herein be incorporated herein by reference).

$D_{1B}$-dopamine receptors of the present invention include proteins homologous to, and having essentially the same biological properties as, the protein coded for by the nucleotide sequence set forth as SEQ ID NO:3. This definition is intended to encompass natural allelic variations in the $D_{1B}$-dopamine receptor sequence, but to exclude the $D_{1A}$-dopamine receptor sequence. Cloned genes of the present invention may code for $D_{1B}$-dopamine receptors of any species of origin, including mouse, rat, rabbit, cat, and human, but preferably code for receptors of mammalian origin. Thus, DNA sequences which hybridize to the sequence given in SEQ ID NO:3 and which code for expression of a $D_{1B}$-dopamine receptor are also an aspect of this invention. Conditions which will permit other DNA sequences which code for expression of a $D_{1B}$-dopamine receptor to hybridize to the sequence given in SEQ ID NO:3 can be determined in a routine manner. Further, DNA sequences which code for polypeptides coded for by the sequence given in SEQ ID NO:3, or sequences which hybridize thereto and code for a $D_{1B}$ receptor, but which differ in codon sequence from these due to the degeneracy of the genetic code, are also an aspect of this invention. The degeneracy of the genetic code, which allows different nucleic acid sequences to code for the same protein or peptide, is well known in the literature. See e.g., U.S. Pat. No. 4,757,006 to Toole et al at Col. 2, Table 1.

The production of cloned genes, recombinant DNA, vectors, host cells, proteins and protein fragments by genetic engineering techniques is well known. See, e.g., U.S. Pat. No. 4,761,371 to Bell et al. at Col. 6 line 3 to Col 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

DNA which encodes the $D_{1B}$-dopamine receptor may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the $D_{1B}$-dopamine receptor gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, $D_{1B}$-dopamine receptor gene sequences may be recovered by use of the polymerase chain reaction (PCR) procedure, with the PCR oligonucleotide primers being produced from the $D_{1B}$-dopamine receptor gene sequence provided herein. See U.S. Pat. Nos. 4,683,195 to Mullis et al. and 4,683,202 to Mullis.

The $D_{1B}$-dopamine receptor may be synthesized in host cells transformed with vectors containing DNA encoding the $D_{1B}$-dopamine receptor. A vector is a replicable DNA construct. Vectors are used herein either to amplify DNA encoding the $D_{1B}$-dopamine receptor and/or to express DNA which encodes the $D_{1B}$-dopamine receptor. An expression vector is a replicable DNA construct in which a DNA sequence encoding the $D_{1B}$ receptor is operably linked to suitable control sequences capable of effecting the expression of the $D_{1B}$ receptor in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the $D_{1B}$ receptor vectors constructed using recombinant DNA techniques. Transformed host cells ordinarily express the $D_{1B}$ receptor, but host cells transformed for purposes of cloning or amplifying the $D_{1B}$ receptor DNA need not express the $D_{1B}$ receptor. When expressed, the $D_{1B}$ receptor will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Suitable host cells include prokaryotes, yeast cells or higher eukaryotic cells. Prokaryotes include gram negative or gram positive organisms, for example *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). Pseudomonas species, Bacillus species, and Serratia marcesans are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al , *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci.* USA 80, 21 (1983)). While these are commonly used, other microbial promoters are suitable. Details concerning nucleotide sequences of many have been published, enabling a skilled worker to operably ligate them to DNA encoding the $D_{1B}$ receptor in plasmid or viral vectors (Siebenlist et al., *Cell* 20, 269 (1980)). The promoter and Shine-Dalgarno sequence (for prokaryotic host expression) are operably linked to the DNA encoding the $D_{1B}$ receptor, i.e., they are positioned so as to promote transcription of the $D_{1B}$ receptor messenger RNA from the DNA.

Eukaryotic microbes such as yeast cultures may be transformed with suitable $D_{1B}$ receptor-encoding vectors. See, U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the $D_{1B}$ receptor, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trpl gene, which provides a selection marker for a mutant strain of yeast lacking the ability to grow in tryptophan, for example ATCC No. 44076 or PEP4-1 (Jones, *Genetics* 85, 12 (1977)). The presence of the trpl lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes may also be ligated into the expression vector 3' of the the $D_{1B}$ receptor coding sequences to provide polyadenylation and termination of the mRNA.

Cultures of cells derived from multicellular organisms are a desirable host for recombinant $D_{1B}$-dopamine receptor synthesis. In principal, any higher eukaryotic cell culture is workable, whether from vertebrate or invertebrate culture, including insect cells. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the human genomic $D_{1B}$ receptor promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the $D_{1B}$ receptor DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, Rachiplusia ou MNPV, or Galleria ou MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

$D_{1B}$-dopamine receptors made from cloned genes in accordance with the present invention may be used for screening compounds for $D_{1B}$ dopamine receptor activity, or for determining the amount of a dopaminergic drug in a solution (e.g., blood plasma or serum). For example, host cells may be transformed with a vector of the present invention, $D_{1B}$-dopamine receptors expressed in that host, the cells lysed, and the membranes from those cells used to screen compounds for $D_{1B}$-dopamine receptor binding activity. Competitive binding assays in which such procedures may be carried out are well known, as illustrated by the Examples below. By selection of host cells which do not ordinarily express a dopamine receptor, preparations free of $D_{1A}$ receptors, $D_2$ receptors, and other dopamine receptor subtypes can be obtained. Further, $D_{1B}$-dopamine receptor agonists and antagonists can be identified by transforming host cells with vectors of the present invention, which host cells also express adenylyl cyclase. Membranes obtained from such cells can be used in biochemical studies wherein the activity of the adenylyl cyclase is monitored. $D_{1B}$ receptor agonists will stimulate the adenylyl cyclase. Such cells must be capable of operatively associating the $D_{1B}$-dopamine receptor with the adenylyl cyclase, i.e., G protein must also be present in the cell membranes. Procedures for carrying out assays such as these are also described in greater detail in the Examples which follow.

Cloned genes and vectors of the present invention are useful in molecular biology to transform cells which do not ordinarily express the $D_{1B}$-dopamine receptor to thereafter express this receptor. Such cells are useful as intermediates for making cell membrane preparations useful for receptor binding assays, which are in turn useful for drug screening. Further, genes and vectors of the present invention are useful in gene therapy. For such purposes, retroviral vectors as described in U.S. Pat. No. 4,650,764 to Temin and Watanabe or U.S. Pat. No. 4,861,719 to Miller may be employed. Cloned genes of the present invention, or fragments thereof, may also be used in gene therapy carried out by homologous recombination or site-directed mutagenesis. See generally K. Thomas and M. Capecchi, *Cell* 51, 503–512 (1987); W. Bertling, *Bioscience Reports* 7, 107–112 (1987); O. Smithies et al., *Nature* 317, 230–234 (1985).

Cloned genes of the present invention, and oligonucleotides derived therefrom, are useful for screening for restriction fragment length polymorphism (RFLP) associated with certain disorders.

Oligonucleotides of the present invention are useful as diagnostic tools for probing $D_{1B}$-receptor gene expression in various tissues. For example, tissue can be probed in situ with oligonucleotide probes carrying detectable groups by conventional autoradiography techniques to investigate native expression of this receptor or pathological conditions relating thereto (e.g., human genetic disorders). This can be done routinely by temperature gradient electrophoresis. In addition, oligonucleotides of the present invention can be used to probe for other $D_{1B}$ receptors or $D_{1B}$ receptors in other species. Further, chromosomes can be probed to investigate the presence or absence of a $D_{1B}$-dopamine receptor gene, and potential pathological conditions related thereto.

Isolated and purified $D_{1B}$-dopamine receptor of the present invention is useful in the rational design of drugs which interact with this receptor. The $D_{1B}$ receptor may be purified from cell membranes or lysed cell fractions containing the receptor, as described above, in accordance with known procedures, including column chromatography (e.g., ion exchange, gel filtration, electrophoresis, affinity chromatography, etc.), optionally followed by crystallization. See generally Enzyme Purification and Related Techniques, *Methods in Enzymology* 22, 233–577 (1977).

The present invention is explained in greater detail in the following examples. These examples are intended to be illustrative of the present invention, and should not be construed as limiting thereof. In the examples, bp means base pair(s); Kb means kilobase; w/v means weight/volume; hr means hour; sec means second; $cm^2$ means square centimeters; $\mu g$ means micrograms; $\mu l$ means microliters; ml means milliliters; mmol means millimoles; means nanomolar; $\mu M$ means micromolar; mM means millimolar; M means Molar; Ci means curies; GBq means gigabecquerels; and temperatures are given in degrees centigrade.

EXAMPLE 1

Polymerase Chain Reaction (PCR) Cloning

Degenerate primers corresponding to the 5th (5'AACCATGGATCCTACATCCCTGTGGCCAT-CATGATTGTCACNTA 3') (SEQ ID NO:1) and 6th (5'CCNCACAAACACACGACAACCGATG-GAAAGAAGCTTAAG ATCAAT 3') (SEQ ID NO:2) transmembrane (TM) regions of the human $D_1$ dopamine receptor described in A. Dearry et al., supra, were used in the polymerase chain reaction (PCR) to amplify sheared human genomic DNA. The PCR products were subcloned into the sequencing vector pBluescript II SK+ (Stratagene), identified by colony lifts using end-labeled oligonucleotides corresponding to TM regions of the human $D_1$ receptor and sequenced using the dideoxy chain termination method as discussed below. One of these products (V-15; 230 bp) displayed a significant homology with the human $D_1$ receptor and corresponded to the 5th TM region, the 3rd intracellular loop and the 6th TM region.

EXAMPLE 2

Genomic Library Screening

The V-15 clone noted in Example 1 above was used as a template for the synthesis of a [$^{32}$P]-labeled probe by PCR. At the end of the reaction, the labeled probe was purified on a Sephadex G-50 column (NICK column; Pharmacia) The purified probe was used to screen $1.5 \times 10^6$ recombinants of a rat testis genomic library in λDASH II. Duplicate nylon filters (Biotrans membranes, ICN) were hybridized in a buffer containing 5×SSC (0.75 M sodium chloride, 0.075 M sodium citrate; pH 7.0), 5×Denhardt's solution (0.1% (w/v) Ficoll, 0.1% (w/v) polyvinylpyrrolidone and 0.1% (w/v) bovine serum albumin), 0.05 M sodium phosphate (pH 7.0), 0.1% SDS, 50% formamide, 200 μg per ml of sheared salmon sperm DNA, and [$^{32}$P]-labeled V-15 probe ($1 \times 10^6$ cpm per ml) at 42° C. for 18-22 hr. At the end of the hybridization period, filters were first washed in a solution containing 2×SSC (0.30 M sodium chloride, 0.03 M sodium citrate; pH 7.0) and 0.1% SDS at room temperature and then washed at 50° C. in a solution containing 0.1×SSC (0.015 M sodium chloride, 0.0015 M sodium citrate, pH 7.0) and 0.1% SDS. Filters were then exposed overnight at −70° C. on Kodak X-OMAT films.

EXAMPLE 3

DNA sequencing

Nucleotide sequencing of both DNA strands was done according to the dideoxy chain termination method (F. Sanger et al., *Proc. Natl. Acad. Sci.* USA 74, 5463-5467 (1977)) by primer extension in pBluescript II SK+ with T7 DNA polymerase (Pharmacia) and $^{35}$S-labeled nucleotide premix ($^{35}$Sequetide; New England Nuclear; Boston, Mass.).

Several clones were isolated and processed for plaque purification using this procedure. A 4.2 kb EcoRI restriction fragment from one clone (DR5) had an open reading frame of 1425 bp (475 aa) which contained the full coding sequence. The calculated molecular weight of this protein is 52834 Da. The nucleotide and predicted amino acid sequence are given together in SEQ ID NO:3, and the predicted amino acid sequence is given separately in SEQ ID NO:4. The putative initiator methionine was selected on the basis of the best Kozak consensus sequence found in frame with the remainder of the coding block and preceded by a stop codon.

COMPARATIVE EXAMPLE A

Structural Comparison with Prior D$_1$ Receptors

Hydropathicity analysis of DR5 (SEQ ID NO:3) revealed the presence of seven stretches of hydrophobic amino acids (data not shown) that may correspond to the seven TM regions typical of G protein-coupled receptors. See B. O'Dowd et al., *Ann. Rev. Neurosci.* 12, 67-83 (1989). At the amino acid level, this putative receptor has about 50% overall identity with the prior art rat and human D$_1$ dopamine receptor. Within TM regions, the DR5 clone has 80% identity with this D$_1$ receptor, whereas the amino and carboxy termini are the most divergent regions (<20% identity). In the TM regions of the rat D$_2$ and D$_3$ dopamine receptors, this identity is only 47% and 39% respectively. Furthermore, two serine residues (Ser 224 and Ser 227) in the 5th TM region and an aspartate residue (Asp 118) in the 3rd TM region are present in this putative receptor, as they are in every cloned catecholamine receptor. These residues have been postulated to be involved in the interaction with the catechol hydroxyl and amino groups of the catecholamines. Putative sites for N-linked glycosylation are found in the amino terminus (asparagine 7) and the 2nd extracellular domain (asparagine 194). A cysteine residue (at position 370) is found in the carboxy tail near the 7th TM region. This residue is conserved in most of the G protein-coupled receptors and has been demonstrated in the β$_2$-adrenergic and rhodopsin receptors to be palmitoylated.

EXAMPLE 4

Expression in Kidney Cells

An expression construct was prepared using the pCMV5 expression vector (B. Cullen, *Methods Enzymol.* 152, 684-704 (1987)) and a 4.2 kb EcoRI restriction fragment of rat clone DR5 (SEQ ID NO:3). African green monkey kidney (COS-7) cells were transiently transfected with the pCMV5-DR5 expression construct by the DEAE-Dextran procedure. B. Cullen, supra. Human embryonic kidney (293) cells were transiently transfected using a calcium-phosphate transfection system (Bethesda Research Laboratories Life Technologies, Inc.).

EXAMPLE 5

Ligand Binding Analysis

Cis-flupentixol, cis-piflutixol, cis-teflutixol were obtained from Lundbeck (Denmark). Fluperlapine was from Novo Nordisk (Bagsvaerd, Denmark). SCH 23388 AND SCH 23390 were obtained from Schering Plough (Bloomfield, N.J.). Apomorphine, (+)butaclamol, dopamine hydrochloride, haloperidol, R(−)- propylnorapomorphine (NPA) and spiperone were purchased from Research Biochemical Industries (RBI). Fenoldopam and SKF 38393 were obtained from Smith, Kline & French. [$^{125}$I]SCH 23982 was from New England Nuclear Boston, Mass.).

COS-7 cells were harvested 48 to 72 hr after transfection. Cells contained in culture flasks (75 cm$^2$) were rinsed with 5 ml of lysis buffer (10 mM Tris-HCl, 5 mM EDTA, pH 7.4). Cells were then scraped and homogenized in lysis buffer for 15 sec using a Brinkman homogenizer. Membranes were centrifuged at 50,000 ×Gravity for 20 min and the pellet was resuspended in binding buffer (50 mM Tris-HCl, 100 mM NaCl, 5 mM EDTA, pH 7.4) Saturation binding studies were performed with increasing concentrations of [$^{125}$I]SCH 23982 (2200 Ci/mmol; 1 Ci=37 GBq). Competition curves were performed with increasing concentrations of unlabeled drug under study against a constant concentration of [$^{125}$I]SCH 233982 (~0.20 nM). The reaction was initiated by adding 100 μl of membranes (~0.45 μg protein) and the assay mixture was incubated in a final volume of 200 μl for 1 hr at room temperature. Assay mixtures were then vacuum-filtered through Whatman GF/C glassfiber filters and washed 3 times with 5 ml of cold washing buffer (50 mM Tris-HCl, 100 mM NaCl, pH 7.2). Total and nonspecific binding were delineated in the absence and presence of 10 μM cis-flupentixol. Each determination was done in triplicate. Bound radioactivity was measured at an efficiency of 75% using a gamma counter (LKB instruments). Binding curves were analyzed using non-linear multiple regression programs. See A. DeLean et al., *Mol. Phar-* macol. 21, 5-16 (1982); G. McPherson, *J. Pharmacol. Methods* 14, 213-228 (1985).

In membranes prepared from COS-7 cells transfected with pCMV5-DR5, the $D_1$ receptor antagonist [$^{125}$I]SCH 23982 was bound to one homogeneous class of binding sites with a dissociation constant ($K_D$) of 0 41±0.01 nM (n=3) This value is similar to the $K_D$ value for this ligand (0.35±0.02 nM, n=2) obtained when the same cells are transfected with the previously characterized $D_1$ dopamine receptor clone (pCMV5-$D_1$ construct). See A. Dearry et al., *Nature* 347, 72-76 (1990). In untransfected or mock transfected COS-7 cells, little or no specific binding was observed. Table 1 summarizes the binding affinities of dopaminergic antagonists and agonists for the binding of [$^{125}$I]SCH 23982 in membranes prepared from COS-7 transfected either with pCMV5-DR5 or pCMV5-$D_1$. The results show that the pharmacological profile at the rat receptor (DR5 clone) is closely related to that observed for the prior human $D_1$ dopamine receptor (the $D_{1A}$ receptor).

TABLE 1

Equilibrium dissociation constant values ($K_D$) of dopaminergic compounds for [$^{125}$I]SCH 23982 binding in COS-7 cell membranes.

| | HUMAN $D_{1A}$ RECEPTOR (nM) | RAT $D_{1B}$ RECEPTOR (nM) | $D_{1B}/D_{1A}$ |
|---|---|---|---|
| ANTAGONISTS | | | |
| SCH 23390 | 0.17 | 0.11 | 0.6 |
| CIS-PIFLUTIXOL | 0.65 | 2 | 3.1 |
| (+)BUTACLAMOL | 1 | 6 | 6.0 |
| CIS-FLUPENTIXOL | 4 | 7 | 1.8 |
| SCH 23388 | 15 | 10 | 0.7 |
| HALOPERIDOL | 24 | 35 | 1.5 |
| CIS-TEFLUTIXOL | 24 | 37 | 1.5 |
| FLUPERLAPINE | 75 | 510 | 6.8 |
| SPIPERONE | 450 | 2600 | 5.8 |
| AGONISTS | | | |
| FENOLDOPAM | 17 | 11 | 0.6 |
| SKF 38393 | 135 | 100 | 0.7 |
| APOMORPHINE | 360 | 240 | 0.7 |
| NPA | 1540 | 1050 | 0.7 |
| DOPAMINE | 12000 | 3900 | 0.3 |

Binding parameters shown are the result of two independent experiments conducted in triplicate determinations. For each drug, the two competition curves were co-analyzed and fitted to a one-site model.

The binding at both receptors was stereoselective since SCH 23390 was about 100 times more potent than SCH 23388. In general, antagonists seemed to be slightly less potent at the rat receptor (DR5 clone) while the agonists appeared to display slightly higher affinities for the rat receptor.

EXAMPLE 6

Adenylyl Cyclase Activity

Adenylyl cyclase activity in 293 cells was measured 72 hr after the transfection. Crude membranes from transfected 293 cells were prepared and resuspended to ~1.25 mg protein/ml in a buffer containing 75 mM Tris-HCl (pH 7.2), 5 mM $MgCl_2$, and 2 mM EDTA (pH 8.0). Adenylyl cyclase activity was assayed in a final volume of 50 μl according to the method previously described. See Y. Salomon et al., *Analyt. Biochem.* 5s, 541-548 (1974).

In 293 cells transiently transfected with the pCMV5-DR5 construct, dopamine and the $D_1$ selective agonist fenoldopam stimulate adenylyl cyclase activity by 2-3 fold (FIG. 1). This effect is blocked by the $D_1$ selective antagonist SCH 23990 but not by the β-adrenergic antagonist alprenolol or the $D_2$ selective antagonist raclopride ($10^{-6}$ M; data not shown). The agonist SKF 38393 ($10^{-6}$ M) also increased the enzyme activity by about twofold.

EXAMPLE 7

Figure 2:
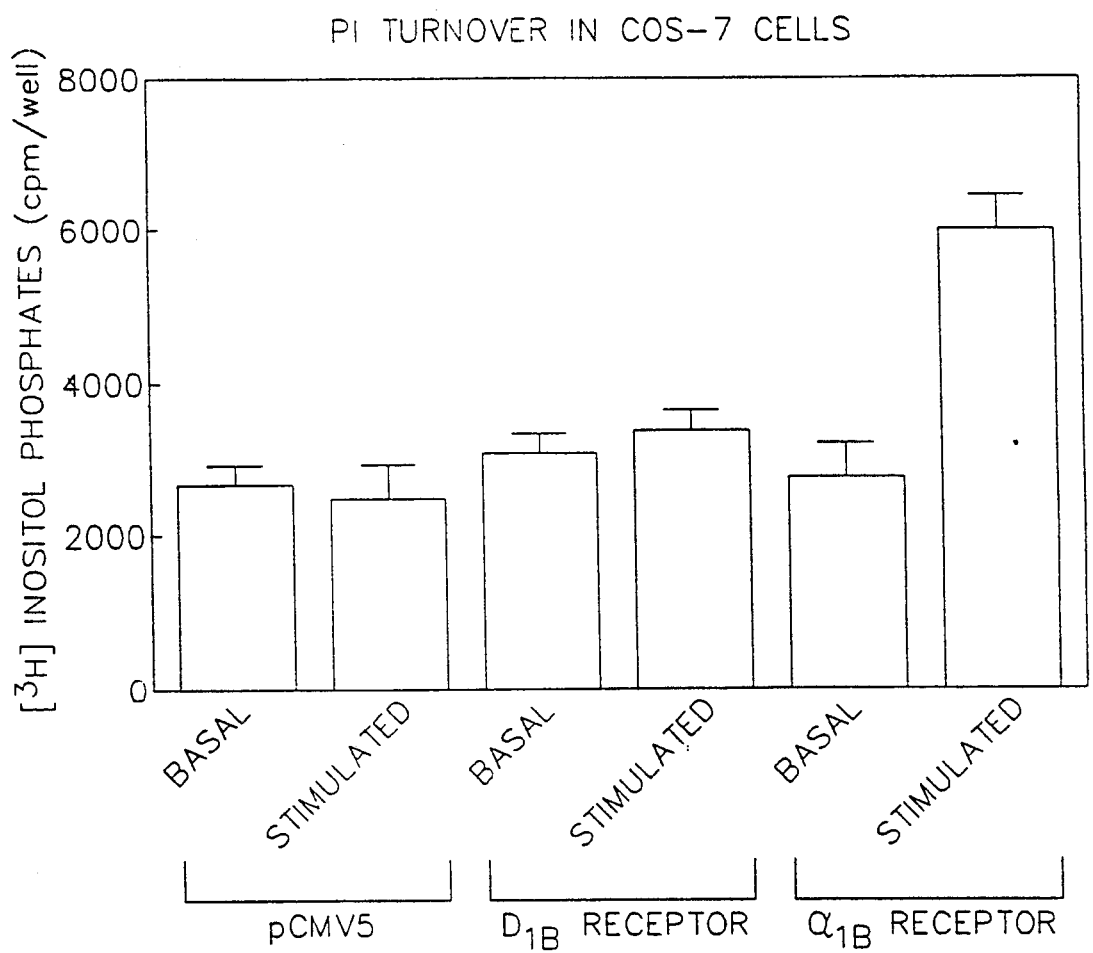
FIG. 2. Inositol phosphate turnover in COS-7 cells. COS-7 cells transfected with pCMV5 alone, pCMV5-DR5 or $\alpha_{1B}$-adrenergic receptor clone were prelabeled overnight with [$^3$H]myo-inositol. Cells were then incubated for 30 min at 37° C. in absence (basal) or presence (stimulated) of agonist. Dopamine (100 μM) was used to elicit a response in cells transfected either with pCMV5 alone or pCMV5-DR5. Norepinephrine (10 μM) was used to stimulate IPs metabolism in cells transfected with the $\alpha_{1B}$-receptor clone. The results shown as mean ±s.e.m., are representative of two independent experiments done in triplicate.

Phosphatidylinositol Turnover 48 hr after transfection, COS-7 cells were labeled overnight with [$^3$H]myo-inositol (18.3 Ci/mmol). [$^3$H]IPs accumulation was assayed as previously described in S. Cotecchia et al., *J. Biol. Chem.* 265, 63-69 (1990). Dopamine did not stimulate IPs turnover in COS-7 cells transiently transfected with the pCMV5-DR5 construct whereas norepinephrine increased IPs metabolism by about 200% in the same cells transfected with the $\alpha_{1b}$-adrenergic receptor clone (FIG. 2). See S. Cotecchia et al., *Proc. Natl. Acad. Sci.* USA 85 7159-7163 (1988).

These results, coupled with those of Example 6, demonstrate that the rat clone DR5 encodes a G protein-coupled receptor which is pharmacologically and biochemically similar to that of the previously cloned $D_1$ dopamine receptor. On this basis we proposed that this receptor be referred to as the $D_{1B}$ subtype whereas the previously cloned $D_1$ receptor would be referred to as the $D_{1A}$ subtype.

EXAMPLE 8

Distribution of $D_{1B}$ Receptor mRNA

Northern Blot Analysis. poly(A)+ RNA was isolated from Sprague-Dawley rat tissues according to the method of Badley et al., *Biotechnique* 6, 114-116 (1988). The RNA was fractionated by electrophoresis on a 1.2% agarose gel containing formaldehyde, transferred onto nylon membranes by capillary blotting, and then hybridized with a specific [$^{32}$P]-labeled probe.

In Situ Hybridization. A 4.2-kb EcoRI restriction fragment from DR5 clone was subcloned into pBluescript II SK+. [$^{35}$S]-Labeled antisense or sense strand RNA probes were prepared by in vitro transcription and rat brain sections were hybridized as previously described. See R. Fremeau et al., *Science* 234, 1265-1269 (1986).

In order to determine the distribution of the $D_{1B}$ receptor mRNA, in situ hybridization, PCR and standard northern blot analyses were carried out in the manner described above. In situ hybridization revealed that this novel $D_1$ dopamine receptor has a distinct mRNA distribution from the one observed for $D_{1A}$ or $D_2$ receptors in rat brain (data not shown). Prominent labeling was found in the lateral mammilary nuclei, the anterior pretectal nuclei and in several layers of the hippocampus. In contrast, no message was detected in striatum, nucleus accumbens and olfactory tubercle; regions in which $D_{1A}$ receptor mRNA is abundant. Furthermore, in the substantia nigra, a region in which $D_2$ receptor mRNA is present, little signal was found for the $D_{1A}$ and $D_{1B}$ receptors. Northern blot analysis of rat tissues revealed two hybridizing bands in hippocampus with estimated sizes of 3.0 and 3.7 kb (data not shown). These two mRNAs are likely derived from the $D_{1B}$ receptor gene since these bands remained even after extensive high-stringency washings (data not shown), and are both distinct from the message for $D_{1A}$ dopamine receptor which has a mRNA size of 4.2 kb. See A. Dearry et al., supra. PCR methodology was used to amplify a specific 339-bp fragment spanning the end of the coding block and 3' untranslated region of the $D_{1B}$ receptor message to detect mRNA that might be present in low abundance in other rat tissues. Consistent with in situ localization, amplified products were detected in the hippocampus and the hypothalamus (data not shown). In the striatum and the cerebellum a weak signal was observed while in the cortex little or no detectable product was amplified. Furthermore, no detectable products were amplified in kidney, heart, lung and liver tissues.

COMPARATIVE EXAMPLE B

Pharmacological and Functional Comparison

The pharmacological and functional characterization of the rat genomic clone DR5 (SEQ ID NO:3) reveal that this gene encodes a G protein-coupled receptor which represents a distinct $D_1$ receptor subtype from the previously cloned rat and human $D_1$ receptors. See A. Dearry et al., Nature 347, 72-76 (1990); Q.Y. Zhou et al., Nature 347, 76-80 (1990). This receptor is referred to as the $D_{1B}$ subtype whereas the previously characterized $D_1$ receptor is referred to as the $D_{1A}$ subtype. Structurally these two receptors are highly homologous, but differ in their amino and carboxy termini as well as in their extracellular and intracellular loops. Phosphorylation of G protein-coupled receptors has been proposed to be important in the regulation of responsiveness of these receptor systems. Comparison of the sequence of the $D_{1A}$ and $D_{1B}$ receptors reveal that, like the $D_{1A}$ receptor which contains several consensus phophorylation sites for protein kinase A (PKA), protein kinase C (PKC) and receptor kinases in every intracellular loop and the carboxy tail, the $D_{1B}$ receptor contains one consensus PKC site in the first intracellular loop, and one and two consensus PKA sites respectively in the 2nd and 3rd cytoplasmic loop. In addition, potential phosphorylation sites for specific receptor kinases exist on the cytoplasmic regions of this receptor.

A distinguishing property of the $D_{1B}$ dopamine receptor is its restricted CNS distribution. The $D_{1A}$ receptor is synthesized most prominently in the striatum, nucleus accumbens, and olfactory tubercle and to a lesser extent in the limbic, cortical, and hypothalamic areas. In contrast, the $D_{1B}$ receptor is expressed in several cell layers of the hippocampus and in two specific sets of nuclei (hypothalamic lateral mammilary and anterior pretectal). This localization implies that this receptor may play a role in the visual relay system, and in the integration of sensory perception. Moreover, the abundance of the mRNA in the hippocampus may suggest a role in memory function.

Heterogeneity within subfamilies of G protein-coupled receptor has been documented for the adrenergic, serotonergic and muscarinic receptors. This multiplicity has been based on distinct pharmacological properties, signal transduction mechanisms, and differences in tissue distribution. As stated before, several lines of evidence had suggested the existence of dopamine receptor subtypes. However, the concept of multiple CNS $D_1$ dopamine receptor subtypes coupled to adenylyl cyclase had not been advanced. Indeed, using the dopamine ligands currently available, this novel receptor subtype could not have been detected previously on the basis of pharmacological properties.

The foregoing examples are illustrative of the present invention, and are not to be construed as limiting thereof. The invention is defined by the following claims, with equivalents of the claims to be included therein.

---

That which is claimed is:

1. An aqueous solution containing cell membranes, said cell membranes containing a $D_{1B}$-dopamine receptor, wherein said $D_{1B}$-dopamine receptor is encoded for by a DNA selected from the group consisting of:
   (a) DNA encoding the rat $D_{1B}$-dopamine receptor having the amino acid sequence given in SEQ ID NO: 4;
   (b) mammalian DNA which selectively hybridizes to a DNA comprising a portion of a gene coding for a $D_{1B}$-dopamine receptor having the amino acid sequence given in SEQ ID NO: 4, wherein said portion does not hybridize to a gene coding for a $D_{1A}$-dopamine receptor under the same hybridization conditions, which mammalian DNA encodes a mammalian $D_{1B}$-dopamine receptor; and
   (c) DNA differing from the DNAs of (a) and (b) above in codon sequence due to the degeneracy of the genetic code, and which encodes a $D_{1B}$-dopamine receptor,
   wherein said cell membranes are free of $D_{1A}$-dopamine receptors.

2. An aqueous solution according to claim 1, said cell membranes further containing adenyly cyclase, and wherein said $D_{1B}$-dopamine receptors are capable of stimulating said adenyly cyclase on binding a $D_{1B}$-dopamine receptor agonist.

3. An aqueous solution according to claim 1, wherein said cell membranes are further free of $D_2$-dopamine receptors.

4. An aqueous solution according to claim 1, wherein said cell membranes are mammalian cell membranes.

5. An aqueous solution according to claim 1, wherein said $D_{1A}$-dopamine receptors are rat $D_{1A}$-dopamine receptors.

* * * * *

UNITED STATES PATENT AND TRADEMARK OFFICE
CERTIFICATE OF CORRECTION

PATENT NO.    : 5,245,011
DATED         : Sep. 14, 1993
INVENTOR(S)   : Mario Tiberi; Keith R. Jarvie; Marc G. Caron It is certified that error appears in the above-identified patent and that said Letters Patent is hereby corrected as shown below:

Column 1, Line 23, after "USA" delete "s7"
    and insert --87--.

Column 8, Line 42, after "millimoles;" delete "means"
    and insert --nMeans--.

Column 11, Line 61, after "Biochem." delete "5s"
    and insert --58--.

Signed and Sealed this

Fifth Day of April, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,245,011
DATED : September 14, 1993
INVENTOR(S) : Mario Tiberi, Keith R. Jarvie, Marc G. Caron It is certified that error appears in the above-identified patent and that said Letters Patent is hereby corrected as shown below:

Column 22, Claim 2, Lines 37 and 39, please correct "adenyly" to read --adenylyl--.

Signed and Sealed this

Seventeenth Day of May, 1994

Attest:

BRUCE LEHMAN

Attesting Officer    Commissioner of Patents and Trademarks